(12) United States Patent
Garric et al.

(10) Patent No.: US 8,013,115 B1
(45) Date of Patent: Sep. 6, 2011

(54) USE OF STABILISED SYNTHETIC COMPOUNDS IN IMMUNOASSAY

(75) Inventors: Isabelle Nathalie Garric, Fontenay-le-Fleury (FR); Isabelle Karine Giuliani, Montpellier (FR); Catherine Christiane Marie Larue, Vaucresson (FR); François Yves Rieunier, Bois D'Arcy (FR); Sylvie Marie-France Trinquier, Strasbourg (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 438 days.

(21) Appl. No.: 10/048,978

(22) PCT Filed: Aug. 14, 2000

(86) PCT No.: PCT/FR00/02323
§ 371 (c)(1),
(2), (4) Date: Feb. 15, 2002

(87) PCT Pub. No.: WO01/13114
PCT Pub. Date: Feb. 22, 2001

(30) Foreign Application Priority Data

Aug. 16, 1999 (FR) .................................. 99 10526

(51) Int. Cl.
*C07K 7/50* (2006.01)
*G01N 33/68* (2006.01)

(52) U.S. Cl. ........ 530/317; 530/324; 530/325; 530/326; 530/327; 530/328; 530/329; 436/86

(58) Field of Classification Search .......... 435/174–182, 435/967, 973, 133.1–135.1, 146.1, 175.1; 436/518, 528–535, 823; 424/193.1–195.11, 424/260.1, 185.1, 192.1–194.1; 530/317, 530/321, 323, 328, 332, 345
See application file for complete search history.

(56) References Cited

U.S. PATENT DOCUMENTS

| 5,106,834 | A | | 4/1992 | Bovy et al. |
| 5,846,738 | A | * | 12/1998 | Seidel et al. ................... 435/7.1 |
| 6,491,923 | B1 | * | 12/2002 | Dave et al. ................. 424/193.1 |
| 6,867,011 | B1 | * | 3/2005 | Babin et al. ................. 435/7.92 |

FOREIGN PATENT DOCUMENTS

| EP | 0 650 053 A1 | 10/1994 |
| WO | WO 92/06996 | 4/1992 |
| WO | WO 96/27661 | 9/1996 |
| WO | WO 98/24816 | 6/1998 |

OTHER PUBLICATIONS

Talbot JA & Hodges RS. Comparative studies on the inhibitory region of selected species of Troponin-l. J. Biol. Chem. 1981;256:12374-12378.*
Talbot JA & Hodges RS. Synthetic studies on the inhibitory region of rabbit skeletal Troponin I. J. Biol. Chem. 1981;256:2798-2802.*
Van Eyk JE & Hodges RS. The biological importance of each amino acid residue of the Troponin I inhibitory sequence 104-115 in the interaction with Troponin C and Tropomyosin-Actin. J. Biol. Chem. 1988;263:1726-1732.*
Wilkinson JM & Grand RJA. Comparison of amino acid sequence of Troponin I from different striated muscles. Nature. 1978;271:31-35.*
Vallins, W.J. et al. Molecular cloning of human cardiac troponin I using polymerase chain reaction. FEBS Letters. 1990;270:57-61.*
Van Eyk, J.E. et al. A comparative study of the interactions of synthetic peptides of the skeletal and cardiac troponin I inhibitory region with skeletal and cardiac troponin C. Biochemistry. 1991;30:9974-9981.*

* cited by examiner

*Primary Examiner* — Anish Gupta
(74) *Attorney, Agent, or Firm* — Jacobson Holman PLLC

(57) ABSTRACT

The invention concerns the use of at least a synthetic compound comprising: a carrier molecule having at least a hydrocarbon chain comprising at least 10, advantageously at least 12, preferably at least 14 and not more than 300, advantageously not more than 100, preferably not more than 50, selected' among C, N, O, S, P and Si, and comprising at least two reactive functions, or capable of reacting, for grafting lateral arms on said chain, and at least two different epitopes carried by said lateral arms grafted on said carrier molecule, as standard or control for immunoassay of said biological molecules, in particular of polypeptides or proteins.

17 Claims, No Drawings

SEQUENCE LISTING

<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Syhthesized

<400> SEQUENCE: 1

Lys Gly Pro Gly Arg Ala Lys Gly
1               5

```
<210> SEQ ID NO 2
<211> LENGTH: 8
<212> TYPE: PRT
<213> ORGANISM: Artificial Sequence
<220> FEATURE:
<223> OTHER INFORMATION: Syhthesized

<400> SEQUENCE: 2

Lys Gly Phe Gly Arg Ala Lys Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Syhthesized

<400> SEQUENCE: 3

Lys Pro Gly Gly Arg Ala Lys Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Syhthesized

<400> SEQUENCE: 4

Lys Phe Gly Gly Arg Ala Lys Gly
1               5

<210> SEQ ID NO 5
<211> LENGTH: 12
<212> TYPE: PRT
<213> ORGANISM: Artificial Sequence
<220> FEATURE:
<223> OTHER INFORMATION: Syhthesized

<400> SEQUENCE: 5

Lys Gly Pro Gly Arg Ala Lys Gly Pro Gly Ser Ala
1               5                   10

<210> SEQ ID NO 6
<211> LENGTH: 35
<212> TYPE: PRT
<213> ORGANISM: Artificial Sequence
<220> FEATURE:
<223> OTHER INFORMATION: Syhthesized

<400> SEQUENCE: 6

Gly Ser Ser Asn Tyr Arg Ala Tyr Ala Thr Glu Pro His Ala Lys Lys
1               5                   10                  15

His Pro Leu Glu Leu Ala Gly Leu Gly Phe Ala Glu Leu Gln Asp Leu
            20                  25                  30

Cys Arg Gln
        35

<210> SEQ ID NO 7
<211> LENGTH: 12
<212> TYPE: PRT
<213> ORGANISM: Artificial Sequence
<220> FEATURE:
<223> OTHER INFORMATION: Syhthesized

<400> SEQUENCE: 7
```

-continued

```
Lys Gly Phe Gly Arg Ala Lys Gly Ser Gly Ser Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Syhthesized

<400> SEQUENCE: 8

Ala Leu Leu Gly Ala Arg
1               5
```

USE OF STABILISED SYNTHETIC COMPOUNDS IN IMMUNOASSAY

This is a 371 of PCT/FR00/02323, filed Aug. 14, 2000, the disclosure of which is incorporated herein by reference.

The present invention relates to synthetic compounds which can be used as standards or controls in immunoassays, in particular for the assay of troponin I, method for preparing them, compositions and kits containing such compounds as well as immunoassay methods using such compounds.

It is known that troponin is a myofibrillar protein complex consisting of three proteins, troponins I, T and C. This protein complex makes it possible to contribute to the regulation of muscle contraction by the $Ca^{2+}$ ion by interacting with myosin and actin. More precisely, it is known that when a nerve impulse arrives at the level of the motor endplate of a muscle, there is generation of an action potential which is transmitted to the sarcoplasmic reticulum. $Ca^{2+}$ is then released into the cytosol and binds to troponin C, which brings about a strengthening of the interaction between troponin I and troponin C and, consequently, a change in conformation of the troponin I, T, C complex. There is then liberation of the sites of actin-myosin interaction, which allows the muscle contraction movement.

When the muscle is damaged, whether it is the cardiac muscle, during myocardial necrosis following a myocardial infarction, or whether it is the skeletal muscle during sustained physical effort, the troponins then released appear more or less rapidly in the blood stream.

Thus, the assay of troponin has recently been recommended for the early diagnosis of myocardial infarction, whether that of troponin T in *Circulation* (1991,) 83, pp. 902-912, or of troponin I in *Am. Heart J.* (1987), 110, pp. 1333-1344, and *Molecular Immunology* (1992), 29 (2), pp. 271-278. Likewise, the assay of cardiac troponin T for measuring the success of thrombolytic therapy following a myocardial infarction has been proposed in *Br. Heart J.*, (1994), 71, pp. 242-248, as well as the assay of skeletal troponin I for the measurement of damage to the skeletal muscles (abstract No. 35 of the *American Association for Clinical Chemistry, 46th National Meeting*, New Orleans, Jul. 17-21, 1994). It should be noted that the assay of the various cardiac and skeletal troponins is nowadays a very useful means for the diagnosis of human and animal pathologies.

It is well known that the immunoassays performed in biological analysis laboratories require the supply by the manufacturer, besides the reagents necessary for the assay (that is to say antibodies, labelled or otherwise, revealing agents and diluting solutions), of a standard for the compound to be determined which, used under conditions similar to those of the sample to be studied, will serve as reference for calculating the results and/or as positive control.

To obtain the standard and/or the control for the compound to be determined, it is possible to use the said compound purified in freeze-dried form (accompanied by a solvent in which the compound will be dissolved by the user before use) or ready for use.

Because biological reagents are unstable, the standard or control solutions prepared from a freeze-dried product are frozen in unit doses and stored at −80° C. It has been observed, moreover, that these solutions were not stable for more than a few hours at +4° C., even if protease inhibitors or antibacterial agents were added to them. This therefore requires the users to prepare their standard solutions immediately before use.

The patent application published under the number FR-A-2,701,954 discloses a stabilized composition of troponin I or T for immunoassay, characterized in that it consists of an aqueous solution containing troponin I or troponin T, mixed with troponin C and particularly in proportions of 1 to molar equivalents of troponin C per equivalent of troponin I or T, and calcium chloride. This technique allows preservation for several days at +4° C. of standard solutions, diluted to a greater or lesser extent, of troponin I or T.

The patent application published under the number FR 2,734,267 describes standard solutions of troponin composed of a ternary complex formed by troponin I, troponin T and troponin C.

The raw materials used to obtain these standards are of human or animal origin, and the standards or controls thus obtained are stable for about one month at +4° C.

Application WO 94/15217 describes some synthetic peptides useful as immunogens for the preparation of antibodies recognizing the N-terminal peptide of troponin I. Some of these peptides can be used as standards in immunoassays of troponin I, using the antibodies which are the subject of the invention covered by application WO 94/15217.

Likewise, patent application WO 94/27156 relates to a method of assaying cardiac troponin I, using antibodies specific for cardiac troponin I. These antibodies can be prepared from peptide fragments having a sequence absent from skeletal muscle troponin I and therefore specific for cardiac troponin I. However, this application neither discloses nor suggests the possibility of using certain peptide fragments as standards in immunoassays of troponin I.

It is also known that application WO 96/27661 describes aqueous solutions for stabilizing proteins and peptides. These solutions find application in particular in diagnostic tests for proteins or peptides.

According to WO 97/27661 these aqueous solutions even make it possible to increase the stability of the fragments of troponin I which are known to be less stable than whole troponin I.

Application EP-A-752 426 published on 8 Jan. 1997 also describes troponin I standards composed of one or more peptides bound to a carrier molecule such as high-molecular weight proteins (>100 KD) or polymers.

Application EP-A-650 053 describes synthetic standards containing active sites for one or more receptors, linked to each other with an arborescent structure. This application describes more particularly synthetic standards for troponin T which are stable in solution for only 3 weeks.

WO 98/24816 describes synthetic biepitopic compounds which can be used as standards in the biological assays of troponin I.

These compounds consist of linear structures comprising two different epitopic peptide sequences of troponin I linked to each other by a linker consisting of a hydrocarbon backbone and/or a peptide backbone, in which the two epitopes may, in addition, be linked by their N- and C-terminal ends, respectively, to additional peptide sequences.

The epitopic synthetic compounds thus obtained exhibit excellent stability in solution, but insufficient linearity of dilution.

The expression "linearity of dilution" is understood to mean the function representing the signal obtained as a function of the dilution factor for the reference compound, which function should be ideally represented by a straight line.

There are known, moreover, with application WO 95/04543, synthetic peptide structures consisting of a matrix of a peptide nature comprising branches formed by branched peptides on the side groups of the matrix peptide via a dendritic linkage.

These branched peptide structures are useful for designing proteins having a defined helical topology.

The work by the inventors which resulted in the present invention has made it possible to discover that branched structures of the type described in WO 95/04543 comprising branched side arms carrying at least two different epitopic sequences of troponin I provided standards or controls for immunoassays for the assay of troponin I exhibiting both high stability in solution at 4° C. and excellent linearity of dilution.

The subject of the invention is the use of at least one synthetic compound comprising:

- a carrier molecule possessing a hydrocarbon chain having at least 10, advantageously at least 12, preferably at least 14 and at most 300, advantageously at most 100, preferably at most 50 atoms chosen from C, N, O, S, P and Si, and comprising at least two functions which are reactive or which are capable of reacting, allowing grafting of side arms onto the said chain; and
- at least two different epitopes carried by the said side arms grafted onto the said carrier molecule, as a standard or control for immunoassays of biological molecules, in particular of polypeptides or proteins.

The hydrocarbon chain may in particular be essentially formed of a succession of $—(CH_2)_n—$ linkages where n is an integer between 10 and 300, advantageously between 10 and 100, preferably between 10 and 50, the said chain being interrupted by one or more heteroatoms or heterogroups such as O, S, N, P and Si, in particular nitrogen-containing heterogroups, and/or substituted with atoms or groups such as halogen, $(C_6-C_{12})$ alkyl, $(C_6-C_{10}$aryl, $(C_6-C_{12})$ aryl-$(C_1-C_n)$alkyl, alkoxy, hydroxyl, aldehyde, $(C_1-C_n)$alkylcarbonyl, amino, thio, carboxyl, oxo, hydroxy-$(C_1-C_{12})$alkyl, thio$(C_1-C_n)$ alkyl, carboxy-$(C_1-C_n)$alkyl, amino$(C_1-C_{12})$alkyl or saturated or unsaturated heterocyclic $C_3-C_{12}$ groups in which the heterocycle is in particular O, S, =N or NR(R being a hydrogen atom or a $C_1-C_{12}$alkyl group), provided that there are present as members interrupting the hydrocarbon chain or substituents of the hydrocarbon chain at least 2 atoms or groups allowing the grafting onto the said hydrocarbon chain of side arms carrying the epitopes in question, in particular amino, hydroxyl, thiol, carboxyl or carbonyl groups.

It is desirable to have a minimum spacing of the functions which are reactive or capable of reacting, on which the side arms carrying epitopes are grafted.

In this regard, it is preferable that the epitopes are spaced apart on the side arms by at least 40 Å, which corresponds to a spacing of at least 9 atoms of the size of the carbon, nitrogen or oxygen atom, or at least three amino acids in the case of a hydrocarbon chain of a peptide nature.

It is preferable, in addition, that the side arms which carry the epitopes are arranged on the carrier molecule so that there is no stearic hindrance or interaction between the said arms, in particular during the immunological reaction of one or more of these epitopes with antibodies.

Advantageously, the side arms are arranged so as to form an angle with each other, it being possible to obtain the latter by introducing a twist or a stiffness into the hydrocarbon chain so that the side arms are arranged in nonparallel, and, preferably opposite, orientations.

The hydrocarbon chain is advantageously an oligopeptide or polypeptide consisting of natural amino acids, such as those found in prokaryotic or eukaryotic proteins, or nonnatural amino acids.

It is preferable in this case for the two consecutive side arms to be carried by two amino acids as defined above, separated from each other by a number 2n+1 amino acids, preferably containing no reactive side chain or containing an inactivated reactive side chain, where n represents an integer and is advantageously between 1 and 6. Preferably, n=2, the values n=3, n=4 and n=5 giving, however, good results.

According to a first embodiment of the invention, the hydrocarbon chain is open and all the atoms of the hydrocarbon chain, in particular of the oligopeptide or polypeptide, form free linkages in rotation, namely which are exocyclic.

In this case, the gap between two consecutive side arms which makes it possible to avoid interactions between the atoms of one side arm with the atoms of the other side arm is obtained when the two consecutive side arms carried by the amino acids correspond to the above spacing condition (i.e. "2n+1").

According to a second embodiment of the invention, the hydrocarbon chain is open and comprises at least one linkage introducing a stiffness into the molecule such that the linkages formed by the atoms of the hydrocarbon chain are no longer all in free rotation.

This may, for example, involve an $sp^2$ carbon atom, for example when the hydrocarbon chain is not, or not exclusively, of a peptide nature, or a carbon atom of a ring.

When the hydrocarbon chain is of a peptide nature, the gap between two consecutive side arms which makes it possible to avoid interactions between the atoms of one side arm with the atoms of the other side arm is obtained by allowing for a gap of 2n+1 amino acids between the amino acids carrying the side arms, n being defined above, or by introducing into the peptide chain a cyclic amino acid generating a stiffness in this chain, or by simultaneously allowing for either of these alternatives.

The stiffness of the carrier molecule may, for example, be conferred by a proline residue.

According to a third embodiment of the invention, the hydrocarbon, in particular oligopeptide or polypeptide, chain is closed so as to form a ring.

A peptide sequence which makes it possible to best satisfy the abovementioned conditions for obtaining the desired gap corresponds to the formula:

$$X_1-A_1-A_2-A_3-A_4-A_5-X_2-A_6$$

in which $X_1$ and $X_2$, which are identical or different, are amino acids carrying the side arms and are chosen from an amino acid with a basic side chain, an amino acid with a negatively charged side chain, an amino acid with a hydroxylated side chain, and an amino acid with a sulphur-containing side chain, $X_1$ and $X_2$ preferably representing lysine, $A_1$ and $A_2$ represent an amino acid chosen from proline, phenylalanine, glycine, alanine, valine, leucine and isoleucine;

with the proviso that one of $A_1$ and $A_2$ is chosen from proline and phenylalanine, $A_3$ represents an amino acid chosen from glycine, alanine, valine, leucine and isoleucine, preferably glycine, $A_4$ represents an amino acid chosen from arginine and histidine, preferably arginine, $A_5$ represents an amino acid chosen from glycine, alanine, valine, leucine and isoleucine, preferably alanine, $A_6$ represents an amino acid chosen from glycine, alanine, valine, leucine, isoleucine, preferably glycine.

Thus, particularly preferred minimum peptide sequences are the sequences:

KGPGRAKG (SEQ ID NO: 1)
KGFGRAKG (SEQ ID NO: 2)
KPGGRAKG (SEQ ID NO: 3) and
KFGGRAKG (SEQ ID NO: 4)

It is preferable that the carrier molecule consists exclusively of linkages of at least 5, advantageously of at least 7 amino acids, and of at most 100, advantageously 50, preferably 30 amino acids, more particularly 20 amino acids in the case of an open chain, and at least 8, preferably at least 10 and at most 100, advantageously 50, preferably 30, more particularly 20 amino acids in the case of a ring, and comprises at last two residues chosen from amino acids with basic side chains, in particular lysine, amino acids with negatively charged side chains, in particular glutamic acid or aspartic acids, amino acids with hydroxylated side chains, in particular serine and threonine, and amino acids with sulphur-containing side chains, in particular cysteine, lysine being [lacuna]. In general, the carrier molecule according to the invention has a molecular mass not exceeding about 10 kilodaltons, preferably not exceeding about 8 kilodaltons. The preferred carrier molecules according to the invention have a molecular mass of less than about 5 kilodaltons. The desired minimum molecular mass is generally about 1 plus or minus 0.2 kilodalton.

The epitopes may consist of any of the epitopes of the biological molecule to be assayed for which antibodies, preferably specific antibodies, exist.

There may be mentioned for troponin I antibodies described by Larue et al. (*Molec. Immunology*, (1992), vol. 20 No. 29, pp. 271-278) Bodor et al. (*Clin. Chem.* (1992), vol 38 No. 11, pp. 2203-2214), Granier et al (*Protein Science*, (1997), vol. 6 suppl. 1, p. 61) and in application WO 94/15217. The majority of these antibodies are commercially available (Hytest LTD-Turku, Finland). The antibodies 11E12 and 8E1 are in particular preferred.

The epitopes are called hereinafter E1 and E2, E1 being different from E2.

The epitopes E1 and E2 may be present as a single copy each on the carrier molecule or as several, in particular two, three or four copies.

In the latter case, the two copies of the same epitope may be present on the same side arm or on two different side arms.

Advantageously, the synthesis of the compounds according to the invention may be rigorously controlled: to ensure the number of epitopes E1 or E2 which were attached to the carrier molecule, the following manual may be used: Synthetic Peptides *A user's guide*, published by Gregory A. Grant, (UWBC Biotechnological Resource Series, Richard R. Burgess series editor), 1992, in Chapter 4: Evaluation of the finished product. See hereinbelow.

It is preferable, however, that the same side arm does not contain more than two identical or different epitopes.

In the case where the epitopes are present in more than two copies, it is preferable that they are carried by as many additional side arms.

When they are present in two copies on the same side arms, the epitopes E1 and E2 are advantageously separated from each other by a linker Z which may be of a peptide or non-peptide nature.

Accordingly, the linker Z may represent:
a peptide sequence of 1 to 40, preferably 3 to 20 amino acids, provided however that the linkage formed by the epitopes and the linker Z do not form together a portion of the sequence of the biological molecule to be assayed, in particular troponin I;
a linear or branched amino $(C_1-C_{10})$alkylcarbonyl chain;
a mixed construct consisting of at least one peptide sequence of 1 to 10 amino acids and at least one linear or branched amino$(C_1-C_{10})$alkylcarbonyl chain.

It is considered that $-E_1-Z-E_2-$ is not part of the sequence of the biological molecule to be assayed, in particular troponin I, when $-E_1-Z-E_2-$ differs from a given fragment of the sequence of the molecule to be assayed, for example troponin I by nonconservative substitution, deletion or insertion of at least one amino acid, preferably of 2 amino acids, more particularly of 5 amino acids.

Z may in particular represent
a chain of formula:

in which m represents an integer from 1 to 10,
or a mixed construct of formulae:

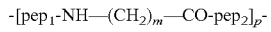

—[NH—$(CH_2)_m$—CO-pep$_2$]$_p$- in which
m represents an integer from 1 to 10,
p represents a integer from 1 to 5, and
pep$_1$ and pep$_2$, which are identical or different, represent a peptide chain containing 2 to 10 amino acids.

The side arms carrying the epitopes preferably comprise, at the N- and C-terminal ends of the epitopes, or of the linkage formed by $E_1-Z-E_2$, additional groups, $Z_1$ and $Z_2$ respectively.

Advantageously, $Z_1$ represents:
a hydrogen atom, an acetyl group, a peptide sequence of 1 to 10 amino acids, an α-acetylated N-terminal peptide sequence of 1 to 10 amino acids, a cysteinyl, biotinyl or biocytinyl group, a peptide sequence of 1 to 10 amino acids carrying a cysteinyl, amino, hydroxyl, halo, carboxyl, biotinyl or biocytinyl residue,
a linear or branched amino $(C_1-C_{10})$ alkylcarbonyl chain,
a linear or branched N-α-acetylated amino$(C_1-C_{10})$alkylcarbonyl chain,
a mixed construct consisting of at least one peptide sequence of 1 to 10 amino acids and at least one linear or branched amino$(C_1-C_{10})$alkylcarbonyl chain, or
a mixed construct consisting of at least one peptide sequence of 1 to 10 amino acids and at least one linear or branched amino$(C_1-C_{10})$alkylcarbonyl chain carrying an amino, halo, hydroxyl, carboxyl, biotinyl, biocytinyl or cysteinyl residue.

Advantageously, $Z_2$ represents:
a hydroxyl radical, an amino radical, a peptide sequence of 1 to 10 amino acids, a peptide sequence of 1 to 10 amino acids carrying a terminal amino, hydroxyl, carboxyl, halo, cysteinyl, biotinyl or biocytinyl group,
a linear or branched amino $(C_1-C_{10})$ alkylcarbonyl chain,
a linear or branched amino $(C_1-C_{10})$ alkylcarbonyl chain carrying a hydroxyl radical or an amino radical,
a mixed construct consisting of at least one peptide sequence of 1 to 10 amino acids and at least one linear or branched amino$(C_1-C_{10})$alkylcarbonyl chain,
a mixed construct consisting of at least one peptide sequence of 1 to 10 amino acids and at least one linear or branched amino$(C_1-C_{10})$alkylcarbonyl chain, carrying a hydroxyl radical or an amino radical.

The side chains are linked to the carrier molecule either directly, or via a spacer which may be a bifunctional group comprising, at its ends, two reactive functions chosen so as to react with the reactive groups carried by the carrier molecule and $Z_1$ or $Z_2$ respectively.

It is preferable for the side arms to comprise epitopes consisting of at most 10, advantageously at most 6 amino acids and for the groups Z, $Z_1$ and $Z_2$ to consist of natural and/or nonnatural amino acids.

The synthetic compounds of the invention may be obtained by a method comprising the following stages:
   stage A: provision of a carrier molecule comprising at least two reactive groups allowing the grafting of side arms,
   stage B: optionally cyclization of the carrier molecule,
   stage C: provision of molecules forming the side arms, comprising at least one function which is reactive with the reactive group of the carrier molecule,
   stage D: coupling of the side arms and of the carrier molecule under appropriate conditions.

When the hydrocarbon chain and the spacers are of a polypeptide nature, the abovedescribed stages may advantageously consist of:
   stage A: provision of an oligopeptide or polypeptide comprising at least two amino acid residues containing at least two identical or different functional side groups (for example: amino).
   In the case of a cyclized peptide, the functional groups are chosen so that there is no interference during the cyclization, or they are temporarily protected using a customary protecting group.
   stage B: possible cyclization of the peptide, either directly, or via a coupling agent.
   For example, in the case of the formation of an amide bond, the coupling may be obtained via the benzotriazolyl-oxy-tris (dimethylamino)phosphonium hexafluorophosphate/1-hydroxybenzotriazol (BOP/HOBt) pair in the presence of a base.
   stage C: provision of the peptides of the unprotected side arms, each carrying a functional group capable of reacting directly or via a coupling agent; and then
   stage D: coupling of the said oligopeptide or polypeptide with the peptides forming the side arms so as to contain the synthetic compound according to the invention.

In a preferred embodiment, the reactive functions of the carrier molecule are amino functional groups, activated via a bifunctional group $_s$SMCC.

In stage D, the bond between a side arm and the carrier molecule is made by a nucleophilic substitution reaction between an —SH residue of the peptide of the said side arm on a maleimide group of the carrier molecule.

The carrier molecule and the side arms are obtained by conventional methods of organic synthesis and/or of peptide chemistry, where appropriate.

The peptides of the carrier molecule and of the side arms carrying the epitopes may be obtained by solid phase synthesis according to conventional methods described by R. B. Merrifield, *J. Amer. Chem. Soc.* (1963), 85, pp. 2149-2154; R. C. Sheppard, in *"Peptides 1971"*, Nesvadba H (ed.) North Holland, Amsterdam, pp. 111; E. Atherton and R. L. Sheppard, in *"Solid phase Peptide synthesis, a practical approach"* IRL PRESS, (1989), Oxford University Press, pp. 25-34.

As automated synthesizer, there may be used the synthesizer "9050 Plus Pep Synthesizer" from Millipore, "Pioneer" from Perspective or the synthesizer "433A" from ABI.

The peptides may also be obtained by homogeneous phase synthesis.

The solid support used for the syntheses should be compatible with the technique and the chemistry used. For example, for a synthesis on the synthesizer "9050 Plus pep. Synthesizer", it is recommended to use a resin suitable for the so-called "continuous flow" technique; the PEG PS resins meet these criteria. These supports consist of a spacer arm based on polyethylene glycol (PEG) situated between the functional group of the polystyrene of the beads and the point of attachment of the first amino acid. The nature of this point of anchorage may vary according to the C-terminal function chosen. For example, for a peptide in the form of an amide, it would be possible to take a resin of the PAL PEG PS type.

The Novabiochem resins also meet the criteria necessary for the continuous flow solid phase synthesis. They have, in addition, the advantage of being able to release the peptide after synthesis under so-called mild acidic conditions, making it possible to obtain peptide fragments in which the side chains of the amino acids are still protected by chemical groups.

The starting resin and the amino acids used as raw material are products which are commercially available (PerSeptiveBiosystem, Perkin-Elmer, Novabiochem).

The side chain protecting groups which may be used are presented in Table I:

TABLE I

| Protecting groups | |
| --- | --- |
| Amino acids | Protecting groups |
| Arginine | 2,2,4,6,7-pentamethyl-5-dihydrobenzofuransulphonyl (Pbf) |
| Asparagine, glutamine | Trityl (Trt) |
| Glutamic acid | Tert-butyl ester (otBu) |
| Threonine, Tyrosine, Serine | Tert-butyl ether (tBu) |
| Lysine | Tert-butyloxycarbonyl (Boc) |

The temporary protection of the primary amine function at the a position of the amino acids may be carried out with the aid of the 9-fluorenylmethyloxycarbonyl (Fmoc) group. The deprotection may be carried out with a 20% piperidine solution in dimethylformamide.

For the coupling, an excess of diisopropylcarbodiimide (DIPCDI) and of 1-hydroxybenzotriazole (HOBt) is preferably used.

For the cyclic peptides constituting the carrier molecule, the Fmoc Ala Nova Syn resin is preferably used.

After synthesis, the resin is washed with organic solvents (dimethylformamide, and then dichloromethane), dried under vacuum and then treated with an acid-based solution.

The peptides thus isolated are then precipitated and rinsed with ether.

For carrier molecules consisting of cyclic peptides, it is possible, for example, to carry out a so-called "head-to-tail" cyclization. For this stage, the peptide is dissolved in DMF, the coupling agent being the BOP/HOBt pair in the presence of a base such as diisopropylethylamine (DIEA), or N-methylmorpholine (NMM). After extraction, the cyclized peptide is precipitated and then washed with an ether-based solution.

The peptide thus obtained is then treated with a trifluoroacetic acid solution and then again precipitated and rinsed with ether.

For carrier molecules of a noncyclic peptide nature, a PAL PEG PS resin is used. After synthesis, the resin is washed with organic solvents (dimethylformamide, dichloromethane), dried under vacuum and then treated with a trifluoroacetic acid-based solution cooled to 0° C. and containing appropriate scavengers. It may be possible to use, for example, the K reagent, containing 82% trifluoroacetic acid, 5% phenol, 5% water, 5% thioanisole and 3% ethanedithiol.

The peptides forming the side arms may be obtained in particular as described in application WO 98/24 816.

The synthetic peptides thus isolated are then precipitated with ether.

The cyclic or linear synthetic compounds are then purified by reversed-phase liquid chromatography and their purity is determined by mass spectrometry. The Bondapak C-18 phase can be used, for example, as phase. The peptides are eluted by means of a linear gradient between two buffer solutions, the first of which is essentially aqueous (for example water-TFA 0.1%) and the second of which is rather organic (for example a mixture containing 60% acetonitrile, 40% water and 0.08% TFA). The pure fractions collected are combined, concentrated under vacuum and freeze-dried, and their purity is checked by mass spectrometry, as indicated in the following manual: Synthetic Peptides *A user's guide*, published by Gregory A. Grant, (UWBC Biotechnological Resource Series, Richard R. Burgess series editor), 1992, in Chapter 4: Evaluation of the finished product.

The functions of the side chains of certain constituent amino acids (for example lysine, arginine, cysteine and the like) of the carrier oligopeptide or polypeptide are then activated with a bifunctional group allowing the specific or non-specific binding of one or more peptides (forming side arms). As example of side chain targeted above which can be used in this type of binding, there may be mentioned the chains carrying amino (primary/secondary), carboxyl, thiol, hydroxide and aldehyde groups, and the like.

As example of compounds comprising bifunctional groups, the following compounds may be used:
   $BS_3$: bis(sulphosuccinimidyl)suberate;
   $_s$SMCC: (sulphosuccinimidyl-4-N-maleimido-methyl)cyclohexane-1-carboxylate;
   BMH: bis-maleidohexane;
   DSG: disuccinimidyl glutarate
   5 MBS: m-maleimidobenzoyl-N-hydroxysulpho succimide ester;
   MPBH: 4-(4-N-maleimidophenyl)butyric acid hydroxide;
   EDC: 1-ethyl-3-(3-dimethylaminopropylate)-carbodiimide.

Using the abovementioned mass spectrometry technique for the final synthetic compounds according to the invention, persons skilled in the art can verify the degree of purity of such a compound. In addition, they can check clearly and unambiguously that the molecular mass of the said compound effectively measured by spectrometry indeed corresponds to the molecular mass expected in the light of the molecular masses of the starting molecules (carrier molecule, epitopes and the like). The present invention therefore allows persons skilled in the art to precisely control the syntheses which they carry out and to know exactly what they are doing.

The subject of the invention is also compounds comprising two different epitopes of troponin I as defined above.

As epitopes of troponin I, there may be mentioned in particular the peptide sequences TEPH; (residues 10-13 of SEQ ID NO: 6), ALLGAR (SEQ ID NO: 8) and FAEL (residues 26-29 of SEQ ID NO: 61 or the sequences comprising the latter.

The subject of the invention is also compositions containing the compounds of the invention comprising at least two epitopes of troponin I.

They are preferably aqueous solutions or compositions consisting of biepitopic synthetic compounds, as described above, in a buffer solution. As buffer solution, there may be used, for example, a phosphate buffer solution ($KH_2PO_4$/$K_2HPO_4$ pH=6.5-7.5) containing Kathon® and bovine serum albumin (BSA), or Kathon®, Régilait® and EDTA, or Kathon®, Plasmion® and optionally EDTA, or Kathon®, casein and EDTA.

It is also possible to use a succinate buffer solution (pH=5-6) or Tris-HCl buffer solution (pH=7.5-8.5) containing Kathon® and bovine serum albumin, or Kathon®, Régilait® and EDTA or Kathon®, Plasmion® and optionally EDTA, or Kathon®, casein and EDTA.

Buffer solutions containing glycine, Kathon®, Régilait® and EDTA may also be used.

The use of a succinate or phosphate buffer solution containing Kathon®, Régilait® and EDTA is preferred.

Kathon®, an antibacterial agent marketed by the company Rohm and Haas, consists of 5-chloro-2-methyl-4-isothiazolin-3-one and 2-methyl-4-isothiazolin-3-one (1.5%).

Régilait© is a skimmed milk powder marketed by the company Régilait (France).

Plasmion® is marketed by Bellon Laboratories (France) and consists of modified fluid gelatine (30 g/l), NaCl (5.382 g/l), $MgCl_2$ (143 mg/l), KCl (373 mg/l), sodium lactate (3.360 g/l), in water.

The following buffer solutions are particularly preferred:
   0.1M succinate buffer solution (pH=6) containing Kathon® (at 0.2%), Régilait (0.05-2%) and 2 mM EDTA,
   0.1M succinate buffer solution (pH=6) containing Kathon® (at 0.2%), casein (0.01-0.5%) and 2 mM EDTA,
   0.1M succinate buffer solution (pH=6) containing Kathon® (at 0.2%) and 1% BSA,
   0.1M phosphate buffer solution $KH_2PO_4$/$K_2HPO_4$ (pH=7.5) containing Kathon® (at 0.2%), Régilait (0.05-0.5%) and 2 mM EDTA,
   0.1M phosphate buffer solution $KH_2PO_4$/$K_2PO_4$ (pH=7.5) containing Kathon® (at 0.2%), casein (0.01-0.1%) and 2 mM EDTA,
   0.1M phosphate buffer solution $KH_2PO_4$/$K_2PO_4$ (pH=7.5) containing Kathon® (at 0.2%), and 1% BSA.

Compositions containing plasma or serum, and a compound of the invention defined above, also form part of the present invention.

Immunoassay methods using, as standards or controls, the compounds as defined above also form part of the invention.

The invention also relates to kits for carrying out immunoassays which include at least one biepitopic compound defined above or at least one composition which contains a biepitopic peptide defined above.

The following examples illustrate the invention and are given without limitations.

EXAMPLE 1

Preparation of Synthetic Biepitopic Compounds According to the Invention

A. Preparation of the Carrier Molecule
A cyclic peptide of the following formula is prepared:

(SEQ ID NO: 5)

```
┌─K GPGRAK GPGSA─┐
│                │
└────────────────┘
```

(peptide 3)

the code being the one-letter code.

This peptide is synthesized on a solid phase by the technique developed in 1963 by Merrifield (J. Am. Chem. Soc. 1963, 85, pp 2149-2154) as described above.

For the synthesis of the above compound, the synthesizer 9050 Plus Synthesizer was used as synthesizer and the Fmoc Ala Nova Syn resin was used as resin. The various stages of the synthesis are summarized in the following Table II:

TABLE II

Stages of the synthesis

| Amino acid residue | NH₂ protection | Side protection | Method of coupling | Number of equivalents/ Duration/ Number of couplings |
|---|---|---|---|---|
| Ser | Fmoc | Tbu | DIPCDI/HOBt | 5 eq/30'/Dc* |
| Gly | " | — | " | " |
| Pro | " | — | " | " |
| Gly | " | — | " | " |
| Lys | " | Boc | " | " |
| Ala | " | — | " | " |
| Arg | " | Pbf | " | " |
| Gly | " | — | " | " |
| Pro | " | — | " | " |
| Gly | " | — | " | " |
| Lys | " | Boc | " | " |

Dc* means double coupling. A double coupling may be carried out in order to increase the purity of the peptide.

At the end of the synthesis, the resin is washed with dimethylformamide, then with dichloromethane and dried under vacuum.

Next, the resin is treated with a solution containing acetic acid, methanol and dichloromethane (5/1/4 V/V/V).

The resin is isolated from the peptide in solution by filtering. The filtrate is concentrated, and the peptide isolated by precipitation with cold ether. 0.145 g of the compound is thus obtained.

The peptide is then cyclized in the following manner:

100 mg of the compound are dissolved in 18 ml of dimethylformamide to which 2 equivalents of BOP, 2 equivalents of HOBt and 5 equivalents of DIEA are successively added.

After two hours of reaction, the cyclized peptide is extracted in a separating funnel.

The organic phase is then dried over Na₂SO₄ and then concentrated in a Rotavapor®, or using any other appropriate rotary evaporator. The cyclized peptide is then precipitated from a mixture of ether, ethylacetate and hexane (6/3/1; V/V/V), for 15 hours at 0° C. 70 mg of cyclized peptide, that is to say 70 mg of carrier molecule, are obtained.

B. Preparation of Biepitopic Synthetic Compounds According to the Invention 8 mg of carrier molecule (i.e. of the above cyclized peptide) dissolved in a DMF/buffer (1/3/2/3) mixture are activated with 6 equivalents of ₛSMCC added dropwise. The reaction is maintained with stirring for about 45 minutes at 18-25° C. The activated carrier molecule is separated from the excess of ₛSMCC by HPLC. The pure fractions are combined and freeze-dried. 4.5 mg of activated carrier molecule are obtained (yield 45%).

2 mg of activated carrier molecule are dissolved in a PBS buffer, pH 6.5. To this solution, there are added 2 equivalents (that is 8 mg) of the following peptide TRP 1116 Ac: Ac-GSSNYRAYA-(TEPH)-AKK-Hx-PLELAGLG-(FAEL)-QDLCRQ-NH₂ (SEQ ID NO: 6)

The peptide sequences in parentheses represent epitopes of troponin I.

The reaction is maintained with stirring for four hours at 18-25° C.

The compound according to the invention thus obtained is then desalted (HPLC/dialysis).

Its molecular mass is evaluated by mass spectrometry (according to the protocol indicated in the manual Synthetic Peptides *A user's guide*, published by Gregory A. Grant, (UWBC Biotechnological Resource Series, Richard R. Burgess series editor), 1992, in Chapter 4: Evaluation of the finished product.

In the same manner, the compounds according to the invention PEP 5, PEP 9 and PEP 10 of the following formulae were prepared:

compound PEP 5:

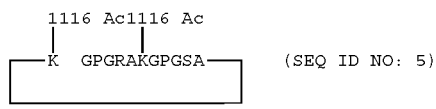 (SEQ ID NO: 5)

compound PEP 9:

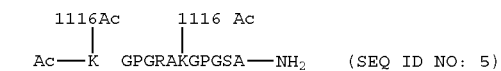 (SEQ ID NO: 5)

compound PEP 10:

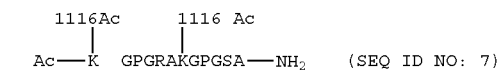 (SEQ ID NO: 7)

in two batches PEP 10 P1 and PEP 10 P2.

The stability and linearity of dilution results for the compounds according to the invention are given below:

EXAMPLE 2

Stability of the compounds according to the invention.

The stability of the compounds PEP 5, PEP 9 and PEP 10 was evaluated by ELISA assay, with chemiluminescence reading (signal expressed in Relative Luminescence Units or RLU), with the aid of the automated device Access® from the company Beckman, distributed by Bio-Rad (Marnes la Coquette, France), and then compared with that of a prior art noncyclized reference biepitopic compound (TRP 1116 Ac) analysed in the same manner.

The results are presented in Table III below.

TABLE III

| | DILUT ABILITY* (BUFFER***) | STABILITY** LIQUID A +4° C. IN BUFFER EXPRESSED BY THE RATIO "signal at DO + X/signal at DO" | | | | | |
|---|---|---|---|---|---|---|---|
| COMPOUND | | DO + 24 H/DO | DO + 1 month/DO | DO + 3 months/DO | DO + 6 months/DO | DO + 9 months/DO | DO + 12 months/DO |
| TRP 1116 Ac | NO | 0.77 | — | — | — | — | — |
| PEP 5 | YES | | 0.94 | 0.89 | 1.06 | 1.04 | 1.03 |
| PEP 9 | YES | | 1.01 | 0.94 | 0.95 | ND | ND |

TABLE III-continued

| COMPOUND | DILUT ABILITY* (BUFFER***) | STABILITY** LIQUID A +4° C. IN BUFFER EXPRESSED BY THE RATIO "signal at DO + X/signal at DO" | | | | | |
|---|---|---|---|---|---|---|---|
| | | DO + 24 H/DO | DO + 1 month/DO | DO + 3 months/DO | DO + 6 months/DO | DO + 9 months/DO | DO + 12 months/DO |
| PEP 10 P1 | YES | | 1.12 | 1.07 | ND | ND | ND |
| P2 | YES | | 1.13 | 1.13 | ND | ND | ND |

*Standard for acceptance of the dilutions: the ratio experimental signal/theoretical signal at a given dilution should be equal to 1.00 ± 0.2 for the compound to be dilutable. The dilutions giving signals of less than 100 000 RLU units should not be taken into account.
**Standard for acceptance of the stabilities: for the stability at day X after DO to be acceptable, it is necessary to obtain a signal at DO + X/signal DO ratio which is equal to 1.00 ± 0.2.
***0.1 M succinate buffer, pH 6.0, containing Kathon at 0.2%, Régilait at 0.2% and 2 mM EDTA (or 0.1 M succinate buffer, pH 6.0, containing Kathon at 0.2% and BSA at 1%).
ND = not determined.

The prior art compound TRP1116 Ac is not stable at DO+24 hours and above, at +4° C.

The compounds according to the invention PEP 5, PEP 9 and PEP 10 are all stable at +4° C. after 3 months, or even 6 months for PEP 9, and 12 months for PEP 5.

EXAMPLE 3

Results of the linearities of the dilution curves.

The results are represented in Table 5 below. Standard for acceptance of the dilutions: the ratio experimental signal/theoretical signal at a given dilution should be equal to 1.00±0.2, for the compound to be dilutable. The dilutions giving signals of less than 100 000 RLU units should not be taken into account.

Results expressed in signal units (RLU)

TABLE 5

| Dilution | Experimental signal (RLU) | Theoretical signal (RLU) | Experimental signal/ theoretical signal |
|---|---|---|---|
| Compound TRP 1116 Ac | | | |
| 1/10 000 | 11 039 697 | | |
| 1/20 000 | 3 779 387 | 5 519 849 | 0.68 |
| 1/40 000 | 1 573 457 | 2 759 924 | 0.57 |
| 1/50 000 | 1 125 417 | 2 207 939 | 0.51 |
| 1/100 000 | 471 714 | 1 103 970 | 0.43 |
| 1/300 000 | 132 054 | 367 990 | 0.36 |
| Compound PEP 5 | | | |
| 1/50 000 | 6 175 137 | | |
| 1/100 000 | 3 175 837 | 3 087 569 | 1.03 |
| 1/200 000 | 1 513 547 | 1 543 784 | 0.98 |
| 1/500 000 | 547 444 | 617 514 | 0.89 |
| 1/1000 000 | 251 103 | 308 757 | 0.81 |
| Compound PEP 9 | | | |
| 1/50 000 | 6 416 384 | | |
| 1/100 000 | 3 411 124 | 3 208 192 | 1.06 |
| 1/200 000 | 1 685 334 | 1 604 096 | 1.05 |
| 1/500 000 | 655 134 | 641 638 | 1.02 |
| 1/1000 000 | 321 101 | 320 819 | 1.00 |
| Compound PEP 10 P1 | | | |
| 1/50 000 | 4 786 295 | | |
| 1/100 000 | 2 433 915 | 2 393 148 | 1.02 |
| 1/200 000 | 1 230 715 | 1 196 574 | 1.03 |
| 1/500 000 | 455 405 | 478 630 | 0.95 |
| 1/1000 000 | 215 853 | 239 315 | 0.90 |
| Compound PEP 10 P2 | | | |
| 1/50 000 | 4 569 989 | | |
| 1/100 000 | 2 287 659 | 2 284 995 | 1.00 |
| 1/200 000 | 1 208 499 | 1 142 497 | 1.06 |
| 1/500 000 | 407 015 | 456 999 | 0.89 |
| 1/1000 000 | 192 408 | 228 499 | 0.84 |

The dilution curves for the compounds according to the invention PEP 5, PEP 9 and PEP 10 still exhibit good linearity, even at high dilutions, unlike the peptide TRP 1116 Ac. Consequently, reliable results can be obtained with the compounds according to the invention: not only do these prove to be of greater stability than the prior art compounds, but also they make it possible to obtain a linear dilution curve. In other words, they solve the problem posed.

The invention claimed is:

1. A synthetic compound consisting of:
   a) a cyclic or noncyclic polypeptide carrier molecule backbone, wherein the cyclic polypeptide carrier molecule backbone consists of 8 to 50 amino acid residues and the noncyclic polypeptide carrier molecule backbone consists of 7 to 50 amino acid residues, containing the sequence:

$X_1$-$A_1$-$A_2$-$A_3$-$A_4$-$A_5$-$X_2$-$A_6$ wherein
   $X_1$ and $X_2$ are lysine residues,
   $A_1$ and $A_2$ represent an amino acid residue selected from the group consisting of proline, phenylalanine, glycine, alanine, valine, leucine, and isoleucine, with the proviso that one of $A_1$ and $A_2$ is selected from the group consisting of proline and phenylalanine,
   $A_3$ represents an amino acid residue selected from the group consisting of glycine, alanine, valine, leucine, and isoleucine,
   $A_4$ represents an amino acid residue selected from the group consisting of arginine and histidine,
   $A_5$ represents an amino acid residue selected from the group consisting of glycine, alanine, valine, leucine, and isoleucine, and
   $A_6$ represents an amino acid residue selected from the group consisting of glycine, alanine, valine, leucine, and isoleucine; and
   b) a side arm grafted to the side chain of each of the two $X_1$ and $X_2$ lysine residues, the side arm carrying at least two different epitopes of human cardiac troponin I.

2. The synthetic compound according to claim 1, wherein one of the amino acid residues A1 and A2 is proline.

3. The synthetic compound according to claim 1, wherein each of the at least two side arms contains more than two different epitopes of human cardiac troponin I.

4. The synthetic compound according to claim 1, wherein $A_3$ represents glycine.

5. The synthetic compound according to claim 1, wherein $A_4$ represents arginine.

6. The synthetic compound according to claim 1, wherein $A_5$ represents alanine.

7. The synthetic compound according to claim 1, wherein $A_6$ represents glycine.

8. The synthetic compound according to claim 1, wherein the polypeptide comprises a sequence selected from the group consisting of:

KGPGRAKG—(SEQ ID NO: 1),
KGFGRAKG—(SEQ ID NO: 2),
KPGGRAKG—(SEQ ID NO: 3), and
KFGGRAKG—(SEQ ID NO: 4).

9. The synthetic compound according to claim 1, wherein each epitope comprises at least a sequence selected from the group consisting of:

TEPH (amino acid residues 10-13 of SEQ ID NO: 6)
ALLGAR, (SEQ ID NO: 8), and
FAEL (amino acid residues 26-29 of SEQ ID NO: 6).

10. The synthetic compound according to claim 1, wherein the carrier molecule backbone is KGPGRAKGPGSA (cyclic) or Ac—KGPGRAKGPGSA—$NH_2$ (SEQ ID NO: 5) or
Ac—KGFGRAKGSGSA—$NH_2$ (SEQ ID NO: 7).

11. A composition containing at least one compound according to claim 1 in solution in water, in plasma, or in a buffer solution.

12. The composition according to claim 11, wherein the buffer solution is selected from the group consisting of phosphate, succinate, and Tris HCl buffer solutions.

13. The composition according to claim 11, wherein the buffer solution is selected from the group consisting of:

succinate buffer solution (pH=5-6) containing 5-chloro-2-methyl-4-isothiazolin-3-one and 2-methyl-4-isothiazolin-3-one, skimmed milk powder and EDTA, succinate buffer solution (pH=5-6) containing 5-chloro-2-methyl-4-isothiazolin-3-one and 2-methyl-4-isothiazolin-3-one, casein and EDTA, succinate buffer solution (pH=5-6) containing 5-chloro-2-methyl-4-isothiazolin-3-one and 2-methyl-4-isothiazolin-3-one and BSA, phosphate buffer solution ($KH_2PO_4/K_2HPO_4$ 0.1 M, pH=6.5-7.5) containing 5-chloro-2-methyl-4-isothiazolin-3-one and 2-methyl-4-isothiazolin-3-one, skimmed milk powder and EDTA, phosphate buffer solution ($KH_2PO_4/K_2HPO_4$ 0.1 M, pH=6.5-7.5) containing 5-chloro-2-methyl-4-isothiazolin-3-one and 2-methyl-4-isothiazolin-3-one, casein and EDTA, and phosphate buffer solution ($KH_2PO_4/K_2HPO_4$ 0.1 M, pH=6.5-7.5) containing 5-chloro-2-methyl-4-isothiazolin-3-one and 2-methyl-4-isothiazolin-3-one and BSA.

14. Immunoassay kit comprising:
at least one synthetic compound as defined in claim 1 and
at least one reagent for carrying out an immunoassay.

15. Immunoassay kit comprising:
at least one composition according to claim 11 and
at least one reagent for carrying out an immunoassay.

16. The synthetic compound according to claim 1, wherein:
the noncyclic polypeptide carrier molecule backbone consists of 7 to 30 amino acid residues.

17. The synthetic compound according to claim 1, wherein:
the cyclic polypeptide carrier molecule backbone consists of 8 to 20 amino acid residues; and
the noncyclic polypeptide carrier molecule backbone consists of 7 to 20 amino acid residues.

\* \* \* \* \*